(12) United States Patent
Samproni

(10) Patent No.: US 11,067,527 B2
(45) Date of Patent: Jul. 20, 2021

(54) SENSOR ASSEMBLY HAVING MICROSENSORS

(71) Applicant: Siemens Healthcare Diagnostics Inc., Tarrytown, NY (US)

(72) Inventor: Jennifer Samproni, Braintree, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 48 days.

(21) Appl. No.: 16/468,929

(22) PCT Filed: Dec. 13, 2017

(86) PCT No.: PCT/US2017/066041
§ 371 (c)(1),
(2) Date: Jun. 12, 2019

(87) PCT Pub. No.: WO2018/112012
PCT Pub. Date: Jun. 21, 2018

(65) Prior Publication Data
US 2020/0096469 A1    Mar. 26, 2020

Related U.S. Application Data

(60) Provisional application No. 62/435,338, filed on Dec. 16, 2016.

(51) Int. Cl.
*G01N 27/27* (2006.01)
*G01N 27/333* (2006.01)
*G01N 33/487* (2006.01)

(52) U.S. Cl.
CPC .......... *G01N 27/27* (2013.01); *G01N 27/333* (2013.01); *G01N 33/48707* (2013.01)

(58) Field of Classification Search
None
See application file for complete search history.

(56) References Cited

U.S. PATENT DOCUMENTS 6,702,857 B2    3/2004    Brauker et al.
2003/0121779 A1*    7/2003    Kidwell ........... G01N 33/48714
204/403.01

(Continued)

FOREIGN PATENT DOCUMENTS

WO    2014089276 A1    6/2014

OTHER PUBLICATIONS

International Search Report and Written Opinion of International Application No. PCT/US2017/066041 dated Feb. 15, 2018.

*Primary Examiner* — J. Christopher Ball
(74) *Attorney, Agent, or Firm* — Dunlap Codding P.C.

(57) ABSTRACT

A system includes a sample analyzer having a sensor assembly. The sensor assembly includes a first microsensor having a first outer sheath, a first membrane core within the first outer sheath, and a first conductive element at least partially encased by and in contact with the first membrane core. The first conductive element detects a first electrical response signal when the first membrane core is in contact with the fluid. The sensor assembly may include a second microsensor that is adjacent to the first microsensor. The second microsensor has a second outer sheath, a second membrane core within the outer sheath, and a second conductive element at least partially encased by and in direct contact with the second membrane core. The second conductive element detects the second electrical response signal when the second membrane core is in contact with the fluid.

14 Claims, 3 Drawing Sheets

(56) References Cited

U.S. PATENT DOCUMENTS

2011/0027913 A1    2/2011   Bau et al.
2015/0233863 A1    8/2015   Say

* cited by examiner

US 11,067,527 B2

SENSOR ASSEMBLY HAVING MICROSENSORS

This application claims priority to U.S. Provisional Application No. 62/435,338, filed Dec. 16, 2016, the disclosure of which is hereby incorporated by reference in its entirety.

TECHNICAL FIELD

The present disclosure is directed to a sensor assembly having one or more microsensors and related systems for analyzing a fluid.

BACKGROUND

Various types of tests related to patient diagnosis and therapy can be performed by analysis of a sample, such as a patient's bodily fluids, using automated sample analyzers. Such sample analyzers obtain measurements from the sample in order to determine the presence and/or amount of analyte of interest. In typical sample analyzers, as the number of analytes for detection increases, the required sample volume increases. Low sample volumes, however, are desirable when the sample is limited, such as in the case of whole blood from neonatal patients or when the sample itself is expensive. Although various known clinical analyzers for chemical, immunochemical and biological testing of samples are available, analytical clinical technology is challenged by increasing needs for improved levels of analysis while reducing sample volume requirements.

SUMMARY

An embodiment of the disclosure is a sensor assembly. The sensor assembly includes a first microsensor having a first outer sheath, a first membrane core within the first outer sheath, and a first conductive element at least partially encased by and in contact with the first membrane core. The first conductive element detects a first electrical response signal when the first membrane core is in contact with the fluid. The sensor assembly may include a second microsensor that is adjacent to the first microsensor. The second microsensor has a second outer sheath, a second membrane core within the outer sheath, and a second conductive element at least partially encased by and in direct contact with the second membrane core. The second conductive element detects the second electrical response signal when the second membrane core is in contact with the fluid.

An embodiment of the disclosure is a system. The system includes a sample analyzer used to analyze a fluid. The sample analyzer includes at least one sensor assembly, at least one transducer coupled the at least one sensor assembly, and a computing device coupled to the at least one transducer. The sensor assembly includes a first microsensor having a first outer sheath, a first membrane core within the first outer sheath, and a first conductive element at least partially encased by and in contact with the first membrane core. The first conductive element detects a first electrical response signal when the first membrane core is in contact with the fluid. The sensor assembly may include a second microsensor that is adjacent to the first microsensor. The second microsensor has a second outer sheath, a second membrane core within the outer sheath, and a second conductive element at least partially encased by and in direct contact with the second membrane core. The second conductive element detects the second electrical response signal when the second membrane core is in contact with the fluid.

BRIEF DESCRIPTION OF THE DRAWINGS

The foregoing summary, as well as the following detailed description of illustrative embodiments of the present application, will be better understood when read in conjunction with the appended drawings. For the purposes of illustrating the present application, there is shown in the drawings illustrative embodiments of the disclosure. It should be understood, however, that the application is not limited to the precise arrangements and instrumentalities shown.

DETAILED DESCRIPTION OF ILLUSTRATIVE EMBODIMENTS

Figure 5:
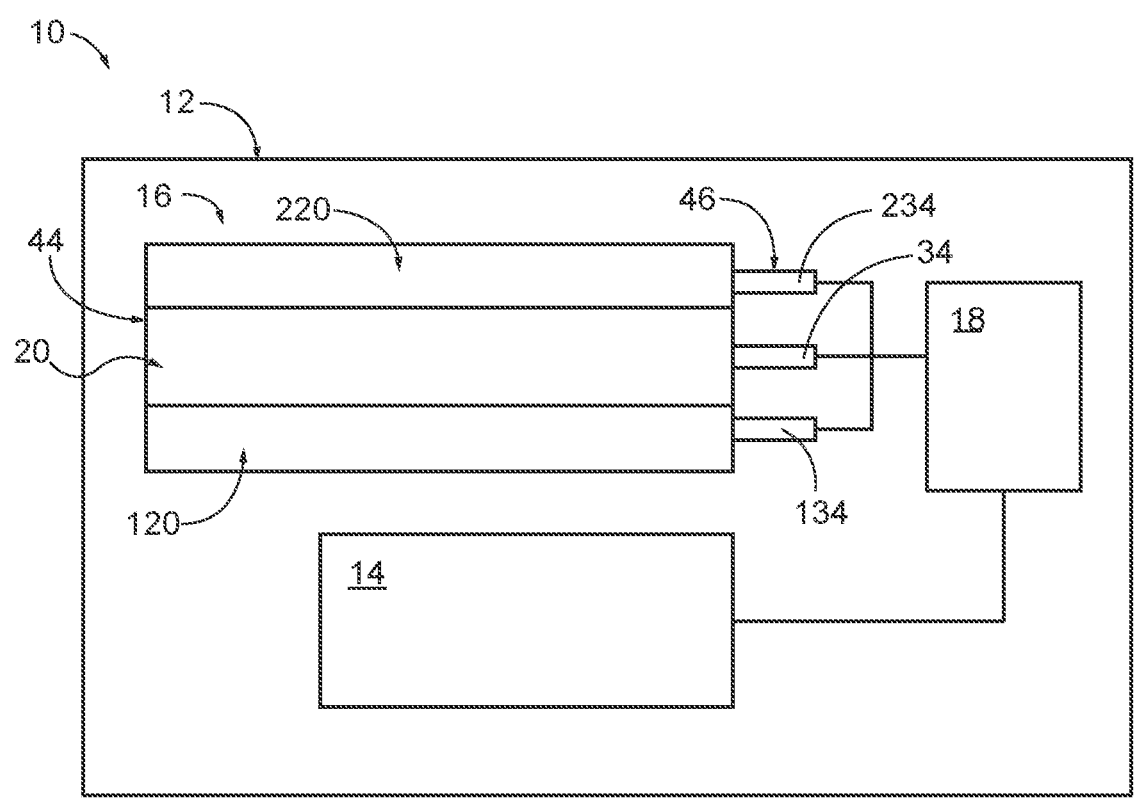
FIG. 5 is a schematic diagram of a system used to analyze a fluid incorporating the sensor assembly shown in FIGS. 1A and 1B.

Turning initially to FIG. 5, an embodiment of the present disclosure includes a test system 10 for analyzing a fluid. The test system 10 includes a sample analyzer 12 configured to analyze signals generated by a sensor assembly 16. The sensor assembly 16 includes one or more sensors 20, 120, 220 that are configured to detect analytes of interest in a sample of the fluid. The sensors 20, 120, 220 may be configured as microsensors that are electrically responsive to a fluid and/or analytes produced by a fluid-reagent reaction. The sensor assembly 16 may be used to test a sample of any particular fluid. For example, the fluid may be a biological fluid, such as whole blood, plasma, pleural fluids, urine, and/or dialysate fluids or other fluids obtained from a patient. Furthermore, the fluid may also include non-biological sample liquids. The fluid is not limited strictly to liquids obtained from a patient.

Analytical tests conducted on the sample are implemented by the sample analyzer 12. The sample analyzer 12 has a computing device 14 and at least one transducer 18 that is electrically coupled to the sensors 20, 120, 220 and to the computing device 14. The transducer 18 forwards electrical response signals generated by the sensor assembly 16 to the computing device 14. The computing device 14 analyzes the electrical response signals generated by the sensor assembly 16.

The computing device 14 includes electrical components that control operation of sample the analyzer 12 and implement analytical techniques for analyzing data generated by the sensor assembly 16. The computing device 14 and its components provide an interface for the user to control operation of the sample analyzer 12. In one example, the computing device 14 has a processing portion (e.g. a computer processor and/or a controller), a memory portion, an input-output portion, a user interface, and one or more software applications. The software application executes instructions for controlling operation of the sample analyzer 12 and its components. The software applications also analyze signals generated by the sensor assembly 16. The computing device 14 may also be configured as a controller. In such an embodiment, the controller may include one or more processors, memory, and input/output links.

The sample analyzer 12 may include dispensing equipment (not shown) used to deliver a sample of fluid to the sensor assembly 16. The dispensing equipment may include a motor that powers an arm controlled by the motor. The arm is adapted to deliver the sample of fluid to the sensor assembly 16 via a pipe, tube, cartridge, insert, or other device for holding a sample. In another embodiment, the dispensing equipment can deliver sample of fluid directly to the sensor assembly 16. In one example, the arm is moveable to deliver the sample of fluid to the sensor assembly 16. Alternatively, the sensor assembly 16 is moveable relative to a fixed arm to receive the sample of fluid. The computing device 14 may include a software application that when executed by the computer processor controls operation of the dispensing equipment.

Figure 1A:
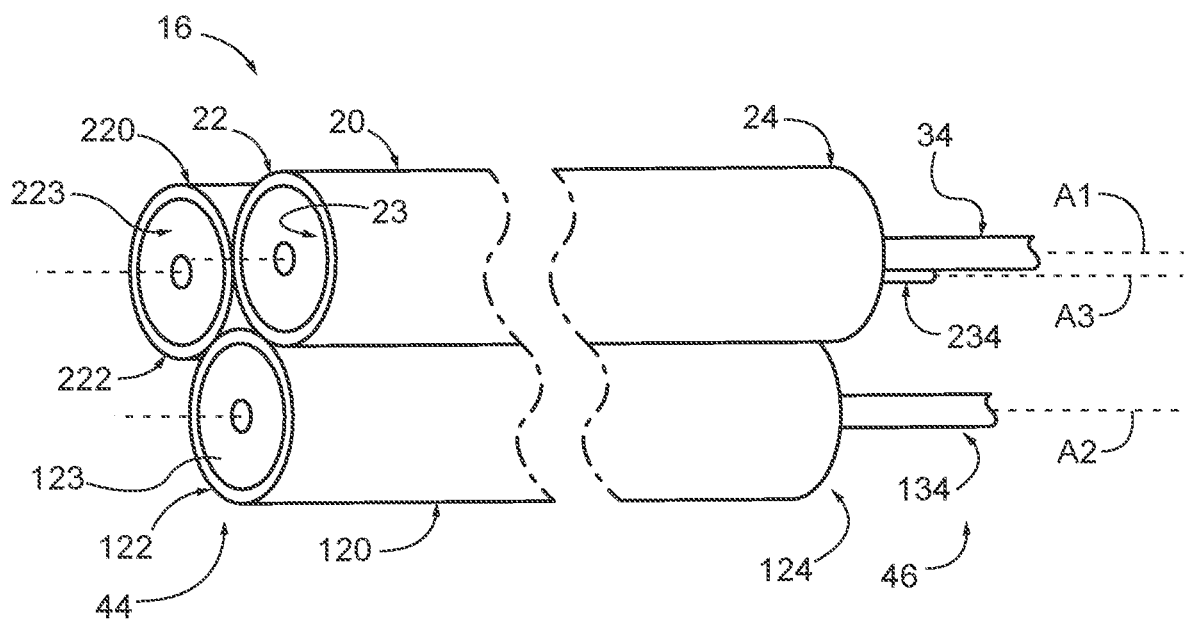
FIG. 1A is a perspective view of a sensor assembly used in a sample analysis system according to an embodiment of the present disclosure.
Figure 1B:
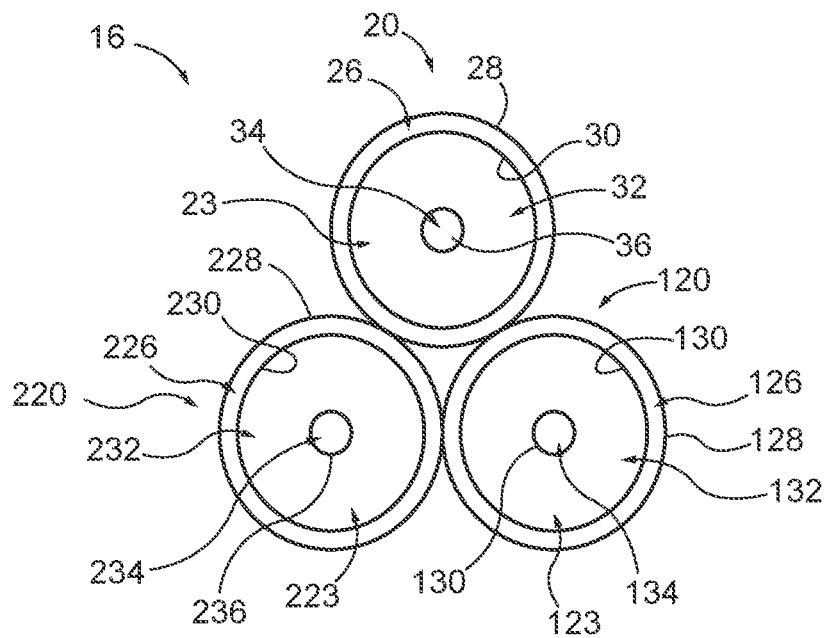
FIG. 1B is an end view of the sensor assembly illustrated in FIG. 1.

Referring to FIGS. 1A and 1B, the sensor assembly 16 includes one or more sensors, such as a plurality of sensors 20, 120, 220. As shown, the sensor assembly 16 has a first microsensor 20, a second microsensor 120, and a third microsensor 220. The first microsensor 20, second microsensor 120, and third microsensor 220 are constructed similarly. However, each sensor may be configured to detect similar analytes or different analytes as further explained below.

In an alternative embodiment, the sensors assembly 16 is remote from the rest of the sample analyzer 12. The sensor assembly 16 can be exposed to a fluid sample by other means, such as manually. In another example, the sensor assembly 16 can be exposed to a fluid sample by inserting the sensor assembly 16 into a stream of flowing sample fluid, such as by insertion into a blood vein of a patient.

Figure 2:
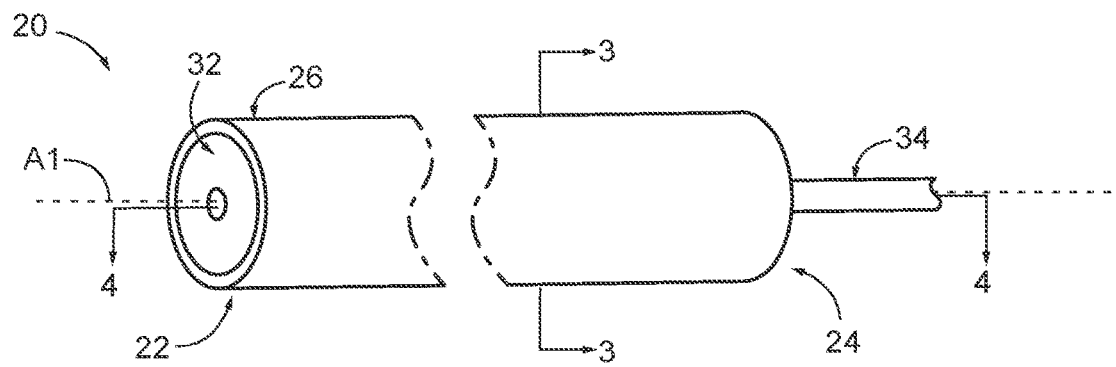
FIG. 2 is a perspective view of a microsensor used in the sensor assembly shown in FIGS. 1A and 1B.
Figure 3:
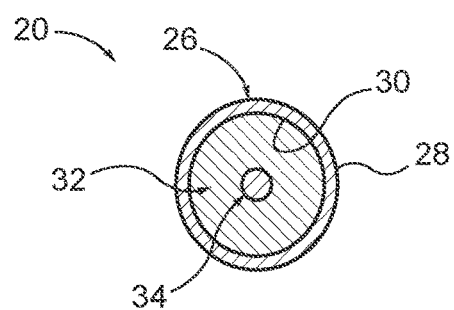
FIG. 3 is a cross-sectional view of the microsensor taken in along line 3-3 in FIG. 2.
Figure 4:
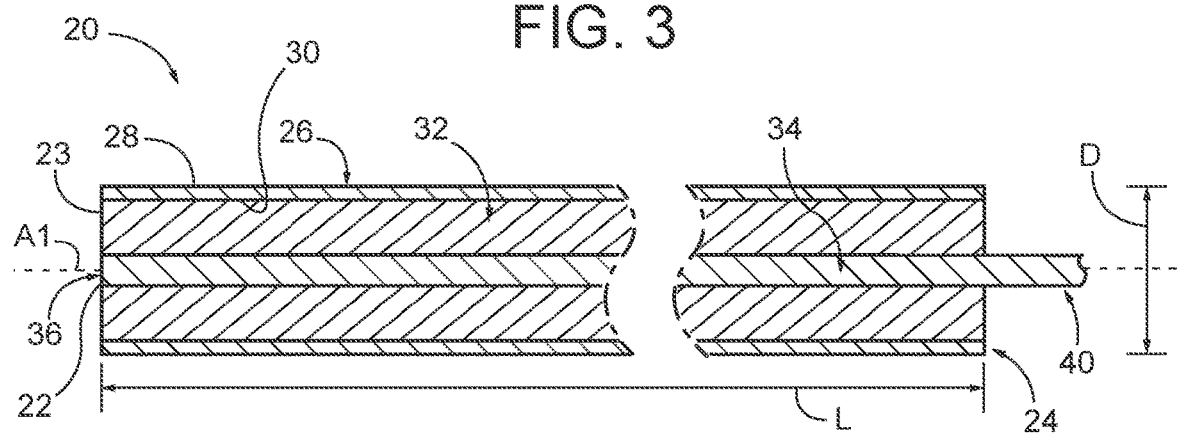
FIG. 4 is a cross-sectional view of the microsensor taken along line 4-4 in FIG. 2.

FIGS. 2-4 illustrate a first microsensor 20 constructed in accordance with the inventive concepts disclosed herein. The first microsensor 20 includes a first outer sheath 26, a first membrane core 32 within the first outer sheath 26, and a first conductive element 34. The first conductive element 34 is at least partially encased by and in contact with the first membrane core 32. In another embodiment, however, the first membrane core 32 does not encase the first conductive element 34. For instance, the first conductive element can be dipped in a membrane so there is a coating of membrane on the end of each sensor 20. The first conductive element 34 can detect and forward the first electrical response signal to the transducer 18 (see transducer 18 in FIG. 5).

Continuing with FIGS. 2-4, the first microsensor 20 has a first end 22 and a second end 24 spaced from the first end along a first axis A1. The first end 22 of the first microsensor 20 defines a first sensor face 23. The first sensor face 23 includes a terminal portion of first membrane core 32 and a terminal end 36 of the first conductive element 34. The first sensor face 23 is positioned to contact the fluid during the test. The first microsensor 20 defines a length L that extends from the first end 22 to the second end 24 along the first axis A1. As shown, the first microsensor 20 is elongated along the first axis A1 and its length L is greater than its cross-sectional dimension D. The cross-sectional dimension D is perpendicular to the length L (and first axis A1). However, the first microsensor 20 can have a length L that is less than or equal to its cross-sectional dimension D. In one example, the cross-sectional dimension D may be between 0.1 mm and about 2.0 mm. However, the cross-sectional dimension D is not limited to this stated range.

Referring to FIGS. 2-4, the first outer sheath 26 defines a first outer surface 28 and a first inner surface 30 that is opposite to the first outer surface 28. The first outer sheath 26 surrounds the first membrane core 32. The first outer sheath 26 may be any material sufficient to contain the first membrane core 32 and the first conductive element 34. The first outer sheath 26 may be formed from glass, a polymer, or a ceramic material such as an oxide of aluminum, silicon or boron. Suitable materials are well known to those skilled in the art. In one embodiment, the first outer sheath 26 is a flexible material. Nonlimiting examples of suitable flexible materials include paper, polyethylene terephthalate (PET), polyethylene (PE), polyimide (PI), polyether ether ketone (PEEK), and the like. The first outer sheath 26 may be in the form of a cylindrical tube. However, the first outer sheath 26 may have any particular cross-sectional shape and the present disclosure is not limited to cylindrical outer sheath 26.

The first membrane core 32 generates an electrical response signal when in contact with the fluid. To achieve this function, the first membrane may be any material that is responsive to a fluid or analyte generated by a fluid-reagent reaction. The first membrane core material may be an ion selective membrane. Suitable ion selective membranes may include an ionophore and a polymer, such as polyvinyl alcohol, polyvinyl chloride, polyvinyl acetate, and/or polyacrylamide, or any other suitable polymer. In some instances, the membrane may include suitable enzymes and/or other components responsive to a particular analyte and/or fluid.

The first conductive element 34 transmits electrical response signals to the transducer 18. The first conductive element 34 may be any conductive material, such as a wire, rod, cable, pin, or the like. The first conductive element 34 can be formed from gold, silver, copper and aluminum metals and alloys thereof, carbon nanotube bundles, and/or another other type of conductive material. The first conductive element 34 extends throughout the length L of the first microsensor 20 and is in contact with the first membrane core 32. In the embodiment shown, the first conductive element 34 has a terminal end 36 and a coupling end 40 that is electrically coupled to the transducer 18 (see FIG. 5). The terminal end 36 is proximate and/or partially defines the first sensor face 23. Furthermore, the first conductive element 34 may be centrally disposed within the first outer sheath 26. In such an example, the first conductive element 34 is coaxial with the first axis A1. In alternative embodiments, the first conductive element 34 may be laterally offset with respect to the first axis A1 and spaced away from the first outer sheath 26. In other embodiments, the first conductive element 34 may be adjacent to the first inner surface 30 of the first outer sheath 26.

The second microsensor 120 and the third microsensor 220 are substantially similar in construction to the first microsensor 20. Referring back to FIGS. 1A and 1B, as shown, the second microsensor 120 includes a second outer sheath 126, a second membrane core 132 within the second outer sheath 126, and a second conductive element 134 at least partially encased by and in contact with the second membrane core 132.

As shown in FIGS. 1A and 1B, the second microsensor 120 has a first end 122 and a second end 124 spaced from the first end 122 along a second axis A2. The first end 122 of the second microsensor 120 defines a second sensor face 123. The second sensor face 123 includes a terminal portion of second membrane core 132 and a terminal end 136 of the second conductive element 134. The cross-sectional dimension (not shown in Figures) of the second microsensor 120 is between 0.1 mm and about 2.0 mm. However, the cross-sectional dimension is not limited to this stated range.

The second outer sheath 126 defines a second outer surface 128 and a second inner surface 130 that is opposite to the second outer surface 128. The second outer sheath 126 surrounds the second membrane core 132. The second outer sheath 126 may be formed from any material sufficient to contain the second membrane core 132 and the second conductive element 134. The second outer sheath 126 may be formed from glass, a polymer, a ceramic material, or any other suitable material known to those skilled in the art.

The second membrane core 132 generates an electrical response signal when in contact with the fluid. The second membrane core 132 may be any material that is responsive to a fluid or analyte generated by a fluid-reagent reaction. Accordingly, the second membrane core may be formed from materials similar to those used form the first membrane core described above. In certain embodiments, the second membrane core material is different from the first membrane core material, such as when the first and second microsensors are designed to detect different analytes.

The second conductive element 134 is at least partially encased by the second membrane core 132. In the embodiment shown, the second conductive element 134 has a terminal end 136 and a coupling end 140 that is electrically coupled to the transducer 18 (see FIG. 5). The terminal end 136 is proximate and/or partially defines the second sensor face 123. The second conductive element 134 may be any conductive material, such as a wire, rod, cable, pin, or the like. The second conductive element 134 may be formed from materials that are similar to those used to form the first conductive element 34.

As shown in FIGS. 2-4, the third microsensor 220 includes a third outer sheath 226, a third membrane core 232 within the third outer sheath 226, and a third conductive element 234 at least partially encased by and in contact with the third membrane core 232. The third microsensor 220 has a first end 222 and a second end 224 spaced from the first end along a third axis A3. The first end 222 of the third microsensor 220 defines a third microsensor face 223. The third microsensor face 223 includes a terminal portion of third membrane core 232 and a terminal end 236 of the third conductive element 234.

The third outer sheath 226 defines a third outer surface 228 and a third inner surface 230 that is opposite to the third outer surface 228. The third outer sheath 226 surrounds the third membrane core 232. The third outer sheath 226 may be formed from any material sufficient to contain the third membrane core 232 and the third conductive element 234. The third outer sheath 226 may be formed from glass, a polymer, a ceramic material or any other suitable material known to those skilled in the art.

The third membrane core 232 generates an electrical response signal when in contact with the fluid. The third membrane core 232 may be any material that is responsive to a fluid or analyte generated by a fluid-reagent reaction. Accordingly, the third membrane core may be formed from materials similar to those used to form the first membrane core and the second membrane core described above. In certain embodiments, the third membrane core material is different from the first and second membrane core materials, such as when the first, second, a third microsensors are designed to detect different analytes.

The third conductive element 234 is at least partially encased by the third membrane core 232. In the embodiment shown, the third conductive element 234 has a terminal end 236 and a coupling end 240 that is electrically coupled to the transducer 18 (see FIG. 5). The terminal end 236 is proximate to and/or partially defines the third microsensor face 223. The third conductive element 234 may be any conductive material, such as a wire, rod, cable, pin, or the like. The third conductive element 234 may be formed from materials that are similar to those used to form the first and second conductive elements 34 and 134.

The sensor assembly 16 may be modified to include as many sensors as needed. FIGS. 1A, 1B, and 5 illustrate three sensors. However, the sensor assembly 16 may have more than three sensors. For example, the sensor assembly 16 may have 2 sensors up to 12 sensors. However, the sensor assembly 16 is not limited to 12 sensors. The sensor assembly 16 may have more than 12 sensors and can detect potentially as many different analytes as there are sensors. In an alternative embodiment, the sensor assembly 16 may comprise one microsensor.

Referring back to FIGS. 1A and 1B, the plurality of sensors 20, 120, 220 are bundled together. Within the bundled sensors, at least two of the plurality of sensors 20, 120, 220 are in contact with each other. In the embodiment illustrated, the first outer surface 28 of the first microsensor 20 is adjacent to the second outer surface 128 of the second microsensor 120. Furthermore, the first outer surface 228 of the third microsensor 220 is adjacent to the second outer surface 128 of the second microsensor 120 and/or the first outer surface 28 of the first microsensor 20. The sensors are arranged with respect to each other so that their respective axes A1, A2, A3 are parallel to each other. In this bundled arrangement, the sensor assembly 16 has a sensing portion 44 and a coupling portion 46. The sensing portion 44 comprises the sensor faces 23, 123, 223 for sensors 20, 120, 220, respectively. The sensor faces 23, 123, 223 may be substantially coplanar as illustrated in FIGS. 1A. However, the sensors 20, 120, 220 and/or sensors faces 23, 123, 223 can be staggered so that the sensor faces 23, 123, 223 are not coplanar to avoid sensor "cross-talk" and reduce interference among the response signals generated by the sensors 20, 120, 220. The sensing portion 44 may contact the fluid to detect the analytes of interest. The coupling portion 46 is opposite the sensing portion 44 and interfaces with the transducer 18 (FIG. 5). In the embodiment shown, the coupling portion 46 is defined by the coupling ends 40, 140, 240 of each sensor 20, 120, 220. The sensing portion 44 can define a relatively small surface area that is responsive to fluid when in contact with the fluid. This, in turn, can reduce the required volume of sample needed to complete the desired analysis. Because of the relatively small sizes of sensors described herein and the potentially large number of sensors that can be bundled together into the sensor assembly 16, large analyte panels can be obtained with relative low sample volume, such as 100 µl or less. For instance, a low sample volume may be less than 100 µl, 80 µl, 60 µl, 40 µl, or 20 µl.

The sensor assembly 16 may can detect a range of analytes. The electrically responsive components of the sensor(s)—the membrane cores--are responsive to fluid upon contact with the fluid. Such fluid responsive sensors may be used to detect a variety of analytes of interest, such as blood gas analytes (e.g. pH, $pCO_2$, $pO_2$), electrolytes ($Na+$, $K+$, $Ca++$, $Cl-$), metabolites (Glucose, Lactate), CO-oximetry (tHb, HHb, $O_2Hb$, $sO_2$, COHb, MetHb), and/or neonatal total bilirubin.

The sensor assembly 16 is adapted to detect various combinations of analytes types. For instance, each sensor (or a set of sensors) may be adapted to detect a different analyte of interest. In still another variation, each sensor (or a set of sensors) may be adapted to detect the same analytes. In accordance with illustrated embodiment, the first membrane core 32 may be electrically responsive to a first analyte. The second membrane core 132 is electrically responsive to a second analyte. The third membrane core 232 is electrically responsive to a third analyte. In one example, each membrane core 32, 132, 232 is responsive to similar analytes (i.e. the first, second and third analytes are the same analytes). Bundling sensors that detect similar analytes provides detection redundancy, thereby improving the reliability of the sensors for that particular analyte. In another example, each membrane core 32, 132, 232 is responsive to different analytes (i.e. the first, second and third analytes are the different analytes). In this case, utilizing membrane cores designed for different analytes increases the breadth of tests available to perform on the sample of fluid.

Manufacture of the sensor assembly 16 involves first forming the sensors and then assembling the sensors into the sensor assembly 16. The sensors may be manufactured by first forming the outer sheath. A membrane solution is inserted into the outer sheath to form the membrane core. Next, a conductive element is inserted into the membrane solution. The membrane solution may cure or solidify into the membrane core. The conductive elements are then coupled to the transducer(s). In some instances, an interface may be coupled to the coupling portion of the sensor assembly 16. The interface electrically connects each conductive element in the sensor assembly 16 to the transducer 18. Any type of interface that can serve this purpose may be used. The sensor assembly 16 may be formed by bundling together a plurality of sensors 20, 120, 220 into an elongate assembly. The sensor assembly 16 may be laterally cut into multiple segments. Because each segment has similar sensors manufactured in common lots, sensor-to-sensor reproducibility over multiple sensor segments is improved.

In use, a sample of fluid is obtained and is inserted into the sample analyzer 12. The fluid contacts the sensing portion 44 of the sensor assembly 16. Each sensor, in turn, generates an electrical response signal that is transmitted to the transducer via the first conductive element 34. The transducer 18, in turn, forwards a signal to the computing device 14. The computing device 14 determines the analytes present in the fluid based on the characteristics of the received signal from the sensors in the sensor assembly 16.

The inventive concepts are not limited in their application to the details of construction and the arrangement of the components set forth in the description or illustrated in the drawings. The inventive concepts disclosed herein are capable of other embodiments or of being practiced or carried out in various ways. Also, it is to be understood that the phraseology and terminology employed herein is for the purpose of description and should not be regarded as limiting the inventive concepts disclosed and claimed herein in any way.

Numerous specific details are set forth in order to provide a more thorough understanding of the inventive concepts. However, it will be apparent to one of ordinary skill in the art that the inventive concepts within the instant disclosure may be practiced without these specific details. In other instances, well-known features have not been described in detail to avoid unnecessarily complicating the instant disclosure.

As used herein, the terms "comprises," "comprising," "includes," "including," "has," "having" or any other variation thereof, are intended to cover a nonexclusive inclusion. For example, a composition, a process, method, article, or apparatus that comprises a list of elements is not necessarily limited to only those elements but may include other elements not expressly listed or inherently present therein.

As used herein the terms "approximately," "about," "substantially" and variations thereof are intended to include not only the exact value qualified by the term, but to also include some slight deviations therefrom, such as deviations caused by measuring error, manufacturing tolerances, wear and tear on components or structures, stress exerted on structures, and combinations thereof, for example.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present). An inclusive or may be understood as being the equivalent to: at least one of condition A or B.

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

Any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

The invention claimed is:

1. A sensor assembly, comprising:
a first microsensor having a first outer sheath defining a first interior space, a first membrane core within the first outer sheath, and a first conductive element that is at least partially encased by and in contact with the first membrane core, the first membrane core filling the interior space between the first outer sheath and the first conductive element, wherein the first conductive element detects a first electrical response signal when the first membrane core is in contact with a fluid; and
a second microsensor adjacent to the first outer sheath of the first microsensor, the second microsensor having a second outer sheath defining a second interior space, a second membrane core within the second outer sheath, and a second conductive element that is at least partially encased by and in contact with the second membrane core, wherein the second conductive element detects a second electrical response signal when the second membrane core is in contact with the fluid.

2. The sensor assembly of claim 1, wherein the first outer sheath defines a first outer surface, and the second outer sheath defines a second outer surface that is in contact with the first outer surface.

3. The sensor assembly of claim 1, wherein the first membrane core is electrically responsive to a first analyte and the second membrane core is electrically responsive to a second analyte that is similar to the first analyte.

4. The sensor assembly of claim 1, wherein the first membrane core is electrically responsive to a first analyte and the second membrane core is electrically responsive to a second analyte that is different from the first analyte.

5. The sensor assembly of claim 1, wherein the first microsensor has a first end and a second end spaced from the first end along a first axis, and the second microsensor has a first end and a second end spaced from the first end of the second microsensor along a second axis, wherein the first axis and the second axis are substantially parallel.

6. The sensor assembly of claim 5, wherein the first end of the first microsensor defines a first sensor face, and the first end of the second microsensor defines a second sensor face that is coplanar with the first sensor face, wherein the first and second sensor faces are adapted to contact to the fluid.

7. The sensor assembly of claim 6, wherein a terminal end of the first membrane core and a terminal end of the first conductive element at least partially define the first sensor face, and a terminal end of the second membrane core and a terminal end of the second conductive element at least partially define the second sensor face.

8. The sensor assembly of claim 1, wherein the first microsensor has a first end and a second end spaced from the first end along a first axis, and the second microsensor has a first end and a second end spaced from the first end of the second microsensor along a second axis.

9. The sensor assembly of claim 8, wherein the first ends of the first and second microsensors are exposed so as to define a sensing portion, wherein the first and second microsensors generate the electrical response signals when the fluid contacts the sensing portion.

10. The sensor assembly of claim 1, further comprising at least one transducer electrically coupled to the first conductive element and the second conductive element.

11. The sensor assembly of claim 1, further comprising a third microsensor that is adjacent to and in contact with at least one of the first microsensor and the second microsensor, wherein the third microsensor has a third outer sheath, a third membrane core within the third outer sheath, and a third conductive element that is at least partially encased by and in contact with the third membrane core, wherein the third conductive element detects a third electrical response signal when the third membrane core is in contact with the fluid.

12. The sensor assembly of claim 11, wherein the third outer sheath defines a third outer surface that is in contact with at least one of the first microsensor and the second microsensor.

13. A system, comprising:
a) a sample analyzer for analyzing a fluid;
b) a sensor assembly, comprising:
a first microsensor having a first outer sheath defining a first internal space, a first membrane core within the first outer sheath, and a first conductive element that is at least partially encased by and in contact with the first membrane core, the first membrane core filling the internal space between the first outer sheath and the first conductive element, wherein the first conductive element detects a first electrical response signal when the first membrane core is in contact with a fluid; and
a second microsensor adjacent to the first outer sheath of the first microsensor, the second microsensor having a second outer sheath defining a second interior space, a second membrane core within the second outer sheath, and a second conductive element that is at least partially encased by and in contact with the second membrane core, the second membrane core filling the internal space between the second outer sheath and the second conductive element, wherein the second conductive element detects a second electrical response signal when the second membrane core is in contact with the fluid; and,
c) a computing device for analyzing electrical response signals generated by the sensor assembly when the sensor assembly is in contact with the fluid.

14. A method for analyzing a fluid, the method comprising:
a) applying a sample of the fluid to a sensing portion of a sensor assembly, the sensor assembly comprising:
a first microsensor having a first outer sheath defining a first internal space, a first membrane core within the first outer sheath, and a first conductive element that is at least partially encased by and in contact with the first membrane core, the first membrane core filling the internal space between the first outer sheath and the first conductive element, wherein the first conductive element detects a first electrical response signal when the first membrane core is in contact with a fluid; and
a second microsensor adjacent to the first outer sheath of the first microsensor, the second microsensor having a second outer sheath defining a second interior space, a second membrane core within the second outer sheath, and a second conductive element that is at least partially encased by and in contact with the second membrane core, the second membrane core filling the internal space between the second outer sheath and the second conductive element, wherein the second conductive element detects a second electrical response signal when the second membrane core is in contact with the fluid;
b) detecting an electrical response signal with the sensor assembly; and
c) analyzing the electrical response signal with the a computing device.

* * * * *